United States Patent [19]

Landi et al.

[11] 4,043,344

[45] Aug. 23, 1977

[54] NON-ABSORBABLE SURGICAL SUTURES COATED WITH POLYOXYETHYLENE-POLYOXYPROPYLENE COPOLYMER LUBRICANT

[75] Inventors: Henry Patrick Landi, Yorktown Heights; Vincent Anthony Perciaccante, Long Island City, both of N.Y.

[73] Assignee: American Cyanamid Company, Stamford, Conn.

[21] Appl. No.: 724,876

[22] Filed: Sept. 20, 1976

[51] Int. Cl.² ............................................. A61L 17/00
[52] U.S. Cl. ............................... 128/335.5; 128/1 R; 428/375
[58] Field of Search ............................ 128/1 R, 335.5; 428/375

[56] References Cited

U.S. PATENT DOCUMENTS

| | | | |
|---|---|---|---|
| 3,061,470 | 10/1962 | Kuemmerer | 428/375 X |
| 3,432,898 | 3/1969 | Stanley et al. | 428/396 X |

*Primary Examiner*—Leland A. Sebastian
*Attorney, Agent, or Firm*—Charles F. Costello, Jr.

[57] ABSTRACT

The handling characteristics, including particularly the knot run down and tissue drag characteristics, of non-absorbable surgical sutures are improved by a coating of a lubricating film of a bioabsorbable copolymer having polyoxyethylene blocks and polyoxypropylene blocks, and which bioabsobable copolymer has a molecular weight such that it is pasty to solid at 25° C. This lubricant coating is absorbed in tissue in less than about 48 hours—which results in improved long term knot security.

17 Claims, 2 Drawing Figures

NON-ABSORBABLE SURGICAL SUTURES COATED WITH POLYOXYETHYLENE-POLYOXYPROPYLENE COPOLYMER LUBRICANT

BACKGROUND OF THE INVENTION

The handling characteristics of surgical sutures encompass many factors, some of which factors are at least in part inconsistent or seemingly inconsistent. There is a constant effort to improve the handling characteristics. Among the more important of the handling characteristics are those associated with knot run-down. In many surgical procedures it is necessary that a knot be tied in a suture when the knot is deep inside a surgical or natural opening. For instance, a dental surgeon may need to tie a knot inside a patients mouth. An intravaginal hysterectomy requires suturing in restricted quarters. One technique frequently used is to tie a square knot that can be run-down from an exterior location where the knot is first tied to lie against tissue with a desired degree of tightness. The knot is snugged down so that it is holding with a degree of firmness chosen by the surgeon for a particular situation and then additional throws are tied down against the first throws of the square knot. In some instances, the first throw is a double twist followed by a single throw to form a surgeons knot, with additional throws to form additional square knots on top as needed. As contrasted with the ease of placement, is the necessity of knot security. Even though it is desired that it be easy to tie a knot, it is mandatory that the knot hold without slipping for an acceptable length of time.

With buried absorbable sutures, the suture including the knot is absorbed, and the knot need only hold until the suture is absorbed. This can be a few hours for certain types of skin incisions, up to 15 to 28 days for some internal knots.

Non-absorbable sutures are used, if strength for a longer time or permanent reinforcement is desired.

Some suture materials are so smooth that a knot run downs very readily and frequently becomes readily untied. Other sutures are of materials in which the knot tends to "lock-up" or refuse to run-down so that it is difficult to snug-down the throws against the tissue and only a few throws are needed, and security is not a problem. Knots in constantly moving tissue, such as adjacent to the heart, particularly if a non-absorbable suture, have a much greater chance of becoming untied than knots in quiescent tissue such as knots holding together a wound inside a plaster cast.

For knots in non-absorbable sutures which are buried in tissue, the problem of knot security for years has been a problem.

PRIOR ART

U.S. Pat. No. 1,254,031 — Jan. 22, 1918, Davis, SUTURE AND METHOD OF MAKING THE SAME, shows a braided collagen suture immersed in collagen or glue to cause close adhesion of the braid, to fill up the interstices and provide a smooth uniform coating.

U.S. Pat. No. 2,576,576 — Nov. 27, 1951, Cresswell and Johnstone, LUBRICATED THREAD, shows a lubricated multifilament collagen thread using as a lubricating film a phosphatide such as lecithin. The lecithin should be applied at the time of coagulation or regeneration of collagen as effective lubrication is not obtained if the lubricant is incorporated by adding to a finished thread.

U.S. Pat. No. 2,734,506 — Feb. 14, 1956 — Nichols et al. SILK SUTURES AND LIGATURES shows using poly(alkyl) methacrylate as a coating for silk sutures, and a hot coating die system.

U.S. Pat. No. 3,187,752 — June 8, 1956 — Glick, NON-ABSORBABLE SILICONE COATED SUTURES AND METHOD OF MAKING, shows silk or other non-absorbable synthetic filaments such as nylon, cotton or linen coated with a silicone which gives a more inert suture and reduces capillarity.

U.S. Pat. No. 3,209,589 — Oct. 5, 1965 — Schlatter, YARN FRICTION MEASURING INSTRUMENT, describes a machine for measuring the friction of a yarn sliding over itself and describes the variation of friction with speed, and the "slip-stick" variety at slow speeds.

U.S. Pat. No. 3,297,033 — Jan. 10, 1967 — Schmitt and Polistina, SURGICAL SUTURES, shows synthetic surgical sutures of polyglycolic acid and discloses that the surfaces of the fiber can be coated with a silicone, beeswax, or the like to modify the handling or the absorption rate.

U.S. Pat. No. 3,390,681 — July 2, 1968, Kurtz, POLYESTER SUTURE HAVING IMPROVED KNOTTING CHARACTERISTICS, shows improving the knotting characteristics of a polyester such as one formed from a dicarboxylic acid and a diol (Dacron) by depositing on the fibers a polytetrafluoroethylene (Teflon). This patent discloses many of the problems in suture knots, and is hereby incorporated by this reference thereto. This patent also shows the accepted practice of classing "ligatures" under "sutures" for patent disclosure purposes.

U.S. Pat. No. 3,565,077 — Feb. 23, 1971, Glick, DENSIFIED ABSORBABLE POLYGLYCOLIC ACID SUTURE BRAID, AND METHOD FOR PREPARING SAME, shows a suture construction using polyglycolic acid filaments with a compacted structure and a reduced void fraction.

U.S. Pat. No. 3,815,315, June 11, 1974, Glick, ETHYLENE OXIDE STERILIZATION OF MOISTURE SENSITIVE SURGICAL ELEMENTS shows the desirability of maintaining surgical elements of polymers subject to the hydrolytic degradation to non-toxic, tissue-compatible, absorbable components, such as polyglycolic acid sutures, in a desiccated condition in an air tight container impervious to moisture vapor. Suitable desiccating cycles and foil containers to give products which are storage stable for years are disclosed.

U.S. Pat. No. 3,867,190 — Feb. 18, 1975, Schmitt and Epstein, REDUCING CAPILLARITY OF POLYGLYCOLIC ACID SUTURES, shows the coating of polyglycolic acid surgical sutures with a copolymer of from 15–85% glycolic acid with 85–15% lactic acid which coating fills the interstices of a multi-filament polyglycolic acid suture. Example 10 discloses the coating as minimizing capillarity, and improving run-down. Thicker coatings increase stiffness. This patent has 38 references to earlier prior art on sutures and methods of making them, and related fields and is incorporated herein by this reference thereto. A divisional of said U.S. Pat. No. 3,867,190 is Ser. No. 489,004, July 16, 1974, REDUCING CAPILLARITY OF POLYGLYCOLIC ACID SUTURES, now U.S. Pat. No. 3,982,543 dated Sept. 28, 1976.

U.S. Pat. No. 3,896,814 — July 29, 1975 — Vivien and Schwartz, COLLAGEN BASED THREADS, shows a collagen or catgut thread which is flexibilized by having therein water and a hygroscopic agent such as a glycerol or a glycol or a low molecular weight (up to 400 m.w.) liquid polyalkalene oxide, and which may additionally be coated with a lipoid or a silicone for surface lubricity.

U.S. Pat. No. 3,942,532 — Mar. 9, 1976 — Hunter and Thompson — BRAIDED SUTURE, discloses an adaptation of an INSTRON Universal Testing Instrument using an oscillographic recorder, to use a single throw between two suture strands to measure surface roughness, as an indication of the ease of sliding a single throw knot down the suture into place, there called "tie-down performance." A coating of 0.4 percent to 7 percent of the suture weight of an aliphatic polyester such as a condensate of adipic acid and 1,4-butanediol having a molecular weight of about 2,000–3,000 is recommended.

U.S. Ser. No. 691,749, filed June 1, 1976 — Casey and Epstein — NORMALLY-SOLID BIOABSORBABLE, HYDROLYZABLE, POLYMERIC REACTION PRODUCT, discloses the use of trans-esterification product of poly(1,4-propylene diglycolate) and polyglycolic acid and other trans-esterification products of polyglycolic acid and a polyester of diglycolic acid and an unhindered glycol to coat sutures to improve knot run-down and other suture characteristics.

The coating, coloring and conditioning of surgical sutures with polymeric materials in general is well-known. Silicones, wax, polytetrafluoroethylene, and other polymers have been used. Specific coating materials with unique advantages to give improved sutures are constantly being sought.

SUMMARY OF THE INVENTION

It has now been found that the knot run-down characteristics, handleability, tie-down performance and tissue drag characteristics of braided, twisted or covered multifilament non-absorbable sutures may be improved by coating with a lubricating biologically absorbable copolymer having polyoxyethylene blocks and polyoxypropylene blocks.

Non-absorbable sutures are sutures which are resistant to biodegradation in living mammalian tissue and remain in the tissue as a foreign body, unless surgically removed (e.g. skin sutures) or extruded. An absorbable suture is degraded in body tissues to soluble products and disappears from the implant site, usually within 2 to 6 months. Non-absorbable sutures retain strength in living mammalian tissue for an extended period, often for the life of the subject. Non-absorbable sutures used for skin closures with the knot above the surface of the skin are removed by the surgeon at a suitable stage of the healing process. For those in which the knot in the non-absorbable suture is buried in living tissue, and are to be left indefinitely, the present lubricant is absorbed from the non-absorbable suture in less than about 48 hours, and hence the lubricating action ceases, and knot security improves.

Non-absorbable sutures are typically of silk, cotton, nylon, a non-absorbable polyester (Dacron ®) polypropylene, polyethylene, or linen. Even metals such as stainless steel, monofilament or braided or tantalum or platinum have been used.

Absorbable or bioabsorbable as applied to the coating, refers to a coating which by hydrolytic or enzymatic degradation, or by its inherent characteristic, has such molecular weight and solubility properties that it is absorbed from the surface of the suture and is eliminated by the subject either unchanged or in hydrolyzed or degraded form.

The lubricant coating not only aids in the knot run-down characteristics but increases the smoothness and flexibility of the sutures so that they may be more easily drawn through the skin and other tissues during placement of the suture. This reduction in friction is called reduced tissue drag. The coating that aids in reduced tissue drag, and lubricates in knot placement also causes the knot to slip more readily.

Another unexpected and unobvious advantage of the present lubricant coating in that the lubricant copolymers are absorbed from the suture within a few days so as the wound heals knot security improves.

The absorbable coating is one or more of a group of compounds having blocks of polyoxyethylene and blocks of polyoxypropylene in their structure. For simplicity and ease of description these compounds are taught, drawn and treated as if there were merely two or three blocks in the chain. However, it is to be understood that non-significant qualities of polyoxypropylene may be present in the polyoxyethylene block and minor quantities of polyoxyethylene may be present in the polyoxypropylene block. From the methods of manufacture it would appear that there may be and probably are such minor admixtures present in the chain. The commercially available grades are acceptable and found to have a low and acceptable degree of toxicity.

The present lubricants may be indicated as having the formula:

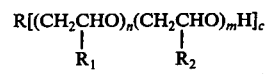

where one of $R_1$ and $R_2$ is methyl and the other hydrogen, and $n$ and $m$ are sufficiently large that the compound is pasty to solid at 25° C., R is the residue of a relatively low molecular weight reactive hydrogen compound having from 2 to about 6 reactive hydrogen atoms and having not over 6 carbon atoms in said compound, and $c$ is the number of reactive hydrogens on the compound forming R. Those compounds which are at least pasty at 25° C. are preferred because they adhere better to the synthetic absorbable polyfilamentary suture. There is not a sharp cut off, but in general as the materials become more pasty or solid, their effectiveness improves.

The lubricant compound and methods of manufacture are described at length in certain prior art. The Pluronics in general are described in U.S. Pat. No. 2,674,619, Apr. 6, 1954, POLYOXYALKYLENE COMPOUNDS, L. G. Lundsted. These are referred to as a cogeneric mixture of conjugated polyoxypropylene-polyoxyethylene compounds and are further described therein.

Certain nitrogen containing polyoxyethylene detergent compositions which are here useful as lubricants are described in U.S. Pat. No. 2,979,528, Apr. 11, 1961, NITROGEN-CONTAINING POLYOXYALKYLENE DETERGENT COMPOSITIONS, L. G. Lundsted. Column 4, lines 44–58 of this patent disclose that the oxypropylene chains may have a small amount of ethyleneoxide therein and vice versa. Because of the sources of ethylene oxide and propylene oxide, usually from petroleum fractions, it is to be expected that in commercial practice complete rectification to chemically pure compounds is not obtained. Fortunately the commercial grades may be used on sutures with excellent results. Said U.S. Pat. No. 2,979,528 also points out that as polymers, all molecular species are far from identical—some chains are shorter, some are longer, but on the average the materials are as indicated and it is the physical properties of the lubricants, not the molecular weight spread of the components, which are important.

U.S. Pat. No. 3,036,118, May 22, 1962, MIXTURES OF NOVEL CONJUGATED POLYOXYETHYLENE-POLYOXYPROPYLENE COMPOUNDS, D. R. Jackson and L. G. Lundsted, has much disclosure on the addition of polyoxyethylene groups and polyoxypropylene groups to reactive hydrogen compounds having from 2 to 6 reactive hydrogen atoms and not over 6 carbon atoms per molecule. Among other such compounds are listed the group consisting of aliphatic polyhydric alcohols, alkylamines, alkylene polyamines, cyclicamines, amides, and polycarboxylic acids, oxyethylene groups and oxypropylene groups. The reactive hydrogen compound serves as a chain initiator and can be present in such a small proportion that it has minor significance in its own right and serves mainly as a foundation on which the predominantly polyoxyethylene or polyoxypropylene blocks may be added in the chosen order. Whereas U.S. Pat. No. 3,036,118 claims primarily the Reverse Pluronics in which the polyoxyethylene chains are attached to the nucleus or initiating reactive hydrogen compounds, in the present invention either the Reverse Pluronic with the polyoxyethylene in the center or the regular Pluronics with the polyoxypropylene in the center or the Tetronics with nitrogen in the center may be used for lubricant purposes.

Because the chemistry is previously known, and to avoid unnecessarily extending the length of the present disclosure, the disclosures of each of these three patents is herein hereby incorporated by this reference thereto.

These lubricating bioabsorbable copolymers are often classed as surface active agents as the polyoxyethylene blocks are predominantly hydrophylic and the polyoxypropylene blocks are predominantly hydrophobic. The materials have been sold by the Wyandotte Chemical Company under the trademark of PLURONICS for the formula:

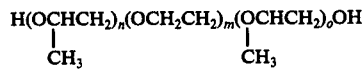

where x, y and z are whole numbers.
REVERSE PLURONICS for the formula:

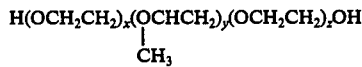

where n, m and o are whole numbers and TETRONICS for the formula:

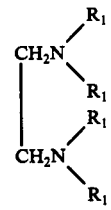

where $R_1$ is

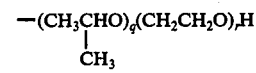

where q and r are whole numbers.

For the present purposes as lubricants for non-absorbable sutures, the values of x, y, z, n, m, o, q and r are such that the lubricants are pasty to solid at 25° C.

The pastes are opaque semi-solids with melting points above room temperature—preferably above about 40° C.

Those classed as Pluronics are particularly useful for the present invention.

The physical characteristics of these lubricant compounds are affected by their total molecular weight and by the percentage of polyoxyethylene in the molecule. References are made to the commercially available compounds for purposes of convenience. Those which are liquid normally have an L as a primary designator, those which are pasty have a P and those which are solid have an F. For the Pluronics, the first number indicates the typical molecular weight of the polyoxypropylene hydrophobic portion with a number 3 being about 950; 4 being about 1200; 5 being about 1450; 6 about 1750; 7 about 2050; 8 about 2250; 9 about 2750; 10 about 3250; 11 about 3625 and 12 about 4000. The second digit indicates the approximate percentage of the polyoxyethylene hydrophylic units in the total molecular, in units of 10. Thus for example, the formulations of certain commercially available products is approximately that shown in Table I.

As all compositions are mixtures, all values are approximate, and values are subject to some rounding.

Additional data is given in The Journal of the American Medical Association, volume 217, pages 469 to 470 (1971) where the new nonproprietary name of POLOXAMER is established for these compositions as direct food additives.

TABLE I

| PLURONIC | Average Molecular Weight | M.W. of each Polyoxyethylene Block | Units of each x and z | % Polyoxyethylene | M.W. of Polyoxypropylene Block | Units of y | M.P. ° C. |
|---|---|---|---|---|---|---|---|
| F-38 | 5000 | 2000 | 46 | 80 | 930 | 16 | 45 |
| F-68 | 8350 | 3300 | 75 | 80 | 1,750 | 30 | 52 |
| F-77 | 6600 | 2300 | 52 | 70 | 2,050 | 35 | 48 |
| P-85 | 4600 | 1200 | 27 | 50 | 2,250 | 39 | 40 |
| F-87 | 7700 | 2700 | 62 | 70 | 2,250 | 39 | 49 |
| F-88 | 10800 | 4300 | 97 | 80 | 2,250 | 39 | 54 |
| F-98 | 13500 | 5400 | 122 | 80 | 2,750 | 47 | 55 |
| F-108 | 14400 | 5600 | 128 | 80 | 3,150 | 54 | 57 |
| F-127 | 12500 | 4300 | 98 | 70 | 3,900 | 67 | 56 |

TABLE I-continued

| REVERSE PLURONIC | | M.W. polyethylene units of m block | | | M.W. polyoxypropylene block | Units of n and O | |
|---|---|---|---|---|---|---|---|
| 10R8 | 3,000 | 2000 | 45 | 65% | 562 | 9 | 46 |
| 17R8 | 4,350 | 2600 | 59 | 60% | 870 | 15 | 53 |
| 25R8 | 9,000 | 3250 | 74 | 57% | 1250 | 22 | 56 |

| TETRONIC | Average Molecular Weight | Approximate Molecular Weight of Individual Polyoxyethylene Block | Approximate % Polyoxyethylene | Molecular Approximate Weight of Individual Polyoxypropylene Block | Approximate % Polyoxypropylene | Average Approximate length of chains per block Units of r | Units of q |
|---|---|---|---|---|---|---|---|
| 707 | 12,000 | 2312 | 74 | 673 | 26 | 52.5 | 11 |
| 908 | 26,100 | 5588 | 85 | 923 | 15 | 127 | 15.9 |
| 1107 | 14,500 | 2438 | 67 | 1173 | 33 | 55.4 | 20.2 |
| 1307 | 18,600 | 3213 | 69 | 1423 | 31 | 73 | 24.5 |
| 1508 | 27,000 | 5063 | 75 | 1673 | 25 | 115 | 28.5 |

In general, the Pluronics with a molecular weight range of from about 4,750 to 16,250 are waxy solids. The polyoxypropylene portion has a molecular weight of 950 to 4,000 and the polyoxyethylene content of about 60–80%.

The pastes in general have a total molecular weight ranging from 3,500 to 5,700 with a polyoxypropylene molecular weight range of 1,750 to 6,500 and polyoxyethylene content of 30 to 50%. The transitions from wax to paste to liquid are not sharp.

COATING

The non-absorbable suture is conveniently coated by several conventional procedures including:

Melt Coating

The uncoated suture is placed in a split die whose orifice corresponds to diameter specifications for the particular size suture to be coated. The die is then clamped in a heating block and the polyoxyethylene-polyoxypropylene lubricant bioabsorbable copolymer placed in the die. The die is raised to a temperature about 20° C. above the melting point of said copolymer and after the copolymer has melted, the suture to be coated is slowly pulled downward through the molten material in the die and collected on a take-up spool. The spool is mounted directly below the die a sufficient distance to allow solidification of the coated. A cooling tunnel or a blast of cooling air may be used to increase production speeds. Nichols et al. U.S. Pat. No. 2,734,506, supra, describes one useful apparatus for coating.

Solution Coating

The polyoxyethylene-polyoxypropylene lubricant bioabsorbable copolymer is dissolved in chloroform. About twice the percentage by weight is used for coating solution as is desired on the final sutures. A feed loop such as a loop of wire or a ceramic is threaded with the uncoated suture, after which the feed loop is then submerged in the solution and the suture is passed down through the feed loop. It may be passed through a die whose diameter is such that after drying a suture will have the desired diameter. The suture is pulled slowly through the solution and at least partially dried in a drying tunnel. The drying is finished after the suture is wound on a spool. Because variations in equipment, speed, and temperature affect the pick-up of the lubricant bioabsorbable polymer, the concentration in the coating is adjusted based on a preliminary run or experience.

Other coating techniques which are well known in the coating of polyfilamentary strands may be used. The techniques used for insulating wire may be adapted for large scale suture manufacture. The above are merely two of the more convenient and well known methods for coating. Details are later illustrated in examples.

TOXICITY

The low toxicity of the polyoxyethylene-polyoxypropylene compounds of the present invention are shown in such U.S. Pats. as U.S. Pat. No. 3,450,502 which describes the use of a copolymer having a total molecular weight of about 8,750 in isotonic solutions used as a priming agent in a heart-lung apparatus. In sutures even if a maximum of around 25–30% by weight of the suture of copolymer is used, only a very small amount is placed in the subject.

The low toxicity is shown in the following table.

TABLE II

TOXICITY

| Pluronic No. | Total Molecular Weight | Physical Characteristic | LD 50 (gm/kg) in Mice |
|---|---|---|---|
| F-38 | 5000 | wax | >5 |
| F-77 | 6600 | wax | 4.2 |
| F-87 | 7700 | wax | 3.75 |
| F-68 | 8350 | wax | >5 |
| F-88 | 10800 | wax | >5 |
| F-127 | 12500 | wax | 2.25 |
| F-98 | 13500 | wax | >5 |
| F-108 | 14400 | wax | 1.25 |
| P-65 | 3400 | paste | 0.83 |
| p-84 | 4200 | paste | 0.4 |
| P-85 | 4600 | paste | 0.53 |
| P-94 | 4600 | paste | 0.6 |
| P-103 | 4950 | paste | 1.4 |
| P-104 | 5850 | paste | 0.75 |
| P-123 | 5750 | paste | 2.7 |
| P-105 | 6500 | paste | 3 |

The polyoxyethylene-polyoxypropylene compositions used as the lubricant bioabsorbable copolymers have been used in food products; and have been the subject of studies as to their elimination from a mammalian body. In general, they are eliminated in the urine fairly rapidly, and within 48 hours nearly all have been eliminated from the blood stream.

If some of the lubricant bioabsorbable copolymer is trapped in braid pores of a suture, the rate of diffusion into the blood stream may be reduced and hence the time for elimination somewhat increased. The molecular weight is small enough that the lubricant bioabsorbable copolymers may be eliminated unchanged, although some degradation may occur before elimination. The important thing is that the lubricant bioabsorbable copolymer has no deleterious effect upon healing tissues adjacent to the sutures, and being removed from the surface of the suture by absorption by the body, knot security is improved. As soon as suture placement is completed, the knot run down and tissue drag reduction function is complete, and as the lubricant bioabsorbable copolymer is removed from the suture, knot security improves.

Definitions in the suture and textile trades are sometimes ambiguous or confused. As herein used;

A "filament" is a single, long, thin flexible structure of a non-absorbable or absorbable material. It may be continuous or staple.

"Staple" is used to designate a group of shorter filaments which are usually twisted together to form a longer continuous thread.

An absorbable filament is one which is absorbed, that is digested or dissolved, in living mammalian tissue.

A "thread" is a plurality of filaments, either continuous or staple, twisted together.

A "strand" is a plurality of filaments or threads twisted, plaited, braided, or laid parallel to form a unit for further construction into a fabric, or used per se, or a monofilament of such size as to be woven or used independently.

The term "suture" is used to include the term "ligature" as technically a suture is used with a needle whereas the ligature is merely used to tie without being placed by a needle.

A finished suture has a needle attached and is sterile and ready for use in surgery. For purposes of convenience in nomenclature, the term "suture" is frequently used to refer to the same strand before it is coated and before it is packaged and sterilized. Context indicates whether it is the sterile suture ready for use, or the suture in a manufacturing step which is referred to.

The strand of the suture is used as the basis for weight in determining the quantity of material that is placed on the non-absorbable strand in forming the non-absorbable surgical suture.

The quantity of the lubricating bioabsorbable copolymer is from about 0.1 to 25 percent by weight of the lubricating bioabsorbable copolymer based on the weight of the uncoated strand forming the suture. It is not necessary that the coating be continuous as a discontinuous coating on the surface aids in reducing friction and chatter. A larger quantity may be present if the lubricating bioabsorbable copolymer penetrates inside the strand, with the various filaments themselves being partially or totally covered.

The wide range of coating weight permits adaptation of the present sutures to many varied uses. Because the strand to be coated to form the suture may have considerable variation in surface roughness, due to the mechanical structure, i.e. braid or twist, etc. as well as being made from filaments which are less than 2 denier per filament to more than 6 denier per filament, with the finer filament sizes giving a smoother surface; and because the filaments may be stretched after the suture is manufactured or in heat treatment, the surface roughness basically can vary. The smoother surfaces require less of the lubricating bioabsorbable copolymer for analogous degrees of slippage.

The various surgical techniques used interact with the desired degree of lubrication. For any given type of knot, a larger quantity of lubricant which for a particular technique increases the ease of run-down, also increases the ease of the knot running back or slipping, called knot security. For some surgical procedures it is highly desirable that the knot be very free in running down, even though the knot slips more readily.

A surgeon in tying knots is confronted with the interaction between the method of tying the knot and the ease of slipping. If a suture is comparatively well lubricated, the surgeon can use a square knot, which is run down readily; with additional squared throws for knot security. On the other hand, if the suture is less well lubricated, the surgeon can use a double half-hitch or some other type of knot which moves more readily to run the knot down to position, after which the double half hitch can be pulled to square the knot, or additional throws can be thrown down against the knot to give adequate knot security. Thus the surgeon can either adapt his knot techniques to a particular suture, or can get sutures whose surface lubricity is best adapted to the technique which the surgeon desires to use. Generally, there is an adaptation of each to the other. The surgeon attempts to get a suture whose characteristics are those which he prefers, and then adapts his knot tying techniques to the sutures that he has at the time. Some surgeons make very successful knots with stainless steel wire using a knotting technique that is adapted to such a wire which has very poor run-down. Others prefer a much more readily run-down well-lubricated suture.

Additionally the location of use has influences. Sometimes a suture in passing through tissue picks up tissue fluids. The suture may be coated with tissue fluids which are either fresh or partly dry at the time the knot is tied. In some surgical techniques it is necessary to preplace the sutures, and tie the suture after the coating of tissue fluids on the suture has a chance to become at least partially dried.

Because the ease of knot run-down and knot security are somewhat opposite, it is necessary for the surgeon to use additional throws or such knots as will hold under the particular conditions of a selected surgical procedure. By changing the quantity of the lubricant bioabsorbable copolymer, the run-down can be modified to suit a using surgeons preference.

The time of use of the knots can be quite varied. Some surgeons use a suture to ligate bleeders in a wound with a retention requirement of 30 minutes or less. Such knots can be removed as the surgical procedure is complete, and before wound closure. Others leave the knots in the tissue even though there is no likelihood that a bleeder would reopen.

Because the present lubricating bioabsorbable copolymer is removed from the suture in living tissue, as the lubricant is removed the knot security increases and after 48 hours more or less, knot security is greatly improved.

The examples following should show the effects of certain different coating and quantities under certain conditions.

The requirements of surgery are extremely varied, and various coating weights permit adaptation of non-absorbable sutures to different conditions.

in general, if the surgeon desires a better lubricated suture, a larger quantity of the lubricating bioabsorbable copolymer is used and conversely if the surgeon is willing to accept slightly reduced knot run-down and tissue drag characteristics in favor of greater knot security, the coating level is reduced in favor of this particular compromise.

Usually from 2 percent to 8 percent of the lubricant bioabsorbable copolymer gives a useful range of compromise between the ease of knot run-down and knot security.

A usage of about 5 percent by weight of Pluronic F-68 is a preferred compromise between the knot rundown and knot security requirements for 2 to 6 denier per filament braided sutures of polyglycolic acid.

The drawings are diagrammatic and representative. The filaments 11 of the non-absorbable suture are at best some what jumbled in actual configuration but are illustrated as patterned in a somewhat idealized style. The coating 12 of the lubricant bioadsorbable polyoxyethylene-polyoxypropylene copolymer is shown much exaggerated. At a level of from 0.1 to 25 percent, the coating would be so thin as to merely be represented by a blurred line if to accurate scale.

Figure 1:
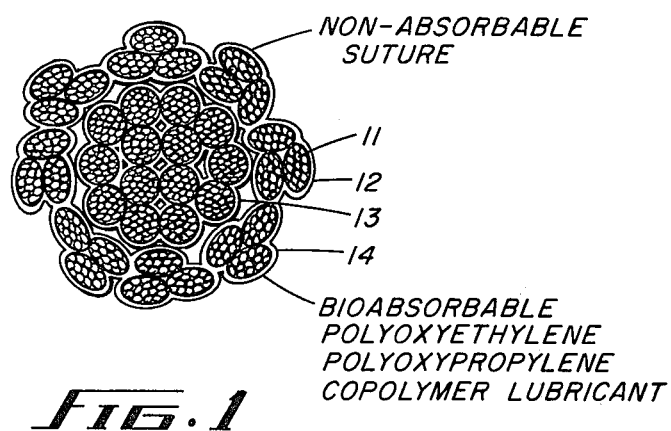
FIG. 1 is cross-section of a non-absorbable suture having on the surface thereof a bioabsorbable polyoxyethylene polyoxypropylene copolymer lubricant.
Figure 2:
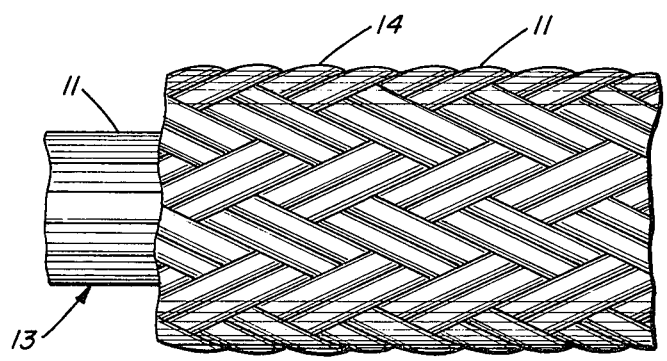
FIG. 2 is a drawing of a suture showing the parallel filaments in the core and the braided sheath. The lubricant coating appears on the surface.

In FIG. 2 the core 13 of the braided suture consists of parallel filaments and the sheath 14 consists of a plurality of filaments, typically braided in configuration. The type of braid shown is representative and diagrammatic. The visability and appearance of the coating varies depending upon the observational technique used to inspect the suture.

The coating 12 in part may bridge the gap between the individual filaments in the finished suture. Depending upon the quantity of coating used, the bridging may be more or less complete but complete filling is not necessary. If the coating level is increased, knot rundown continues to be improved, but knot security is compromised.

Also 5 runs were made using a commercial silicone coated silk suture, see U.S. Pat. No. 3,187,752, supra, for comparative purposes.

For these coatings, the braid was run through a solution of the Pluronic in chloroform at a concentration of about twice the percentage desired for the coating on the suture, and air dried.

A standard ATLAB yarn Friction Tester Model CS-152-026, Custom Scientific Instruments, Inc. Whippany, New Jersey 07981, with a Hewlett Packard Model 321 dual channel amplifier recorder was used to record the tension of the strand feeding into the tester, and coming out of the yarn tester. The chatter factor is the ratio of maximum pull ($T_3$) to the feed tension ($T_1$) minus the minimum pull ($T_2$) to the feed tension, i.e.($T_3/T_1$) − ($T_2/T_1$). The values for friction are of ($T_2/T_1$) to start slipping.

The values of particular interest are the ratios and percent reduction. With other types of test devices, the numerical values may change, but the relative ratios as an index of improvement are analogous.

In this test, an uncut strand, coated as indicated, was used for the test. For use as a suture, such strand is cut to length, needled, packaged and sterilized using conventional techniques. The friction and chatter is more readily measured on continuous lengths.

Reduction in static friction, chatter and the coefficient of friction are shown in Table III.

TABLE III

| Run No. | Pluronic Coating | Level (%) | Static Friction | Size 2/0 Silk Braid % Reduction | Chatter Factor | % Reduction | Coeff. of Friction × $10^{-2}$ | % Reduction |
|---|---|---|---|---|---|---|---|---|
| 1 | Blank | — | 3.15 | — | 0.46 | — | 6.300 | — |
| 2 | Blank | — | 3.40 | — | 0.47 | — | 6.822 | — |
| 3 | Blank | — | 3.32 | — | 0.46 | — | 6.690 | — |
| 4 | Blank | — | 3.78 | — | 0.93 | — | 6.666 | — |
| 5 | Silicone | — | 3.75 | — | 0.66 | — | 7.203 | — |
| 6 | Silicone | — | 3.60 | — | 0.63 | — | 6.930 | — |
| 7 | Silicone | — | 3.63 | — | 0.74 | — | 6.756 | — |
| 8 | Silicone | — | 3.63 | — | 0.63 | — | 7.015 | — |
| 9 | Silicone | — | 3.56 | — | 0.89 | — | 6.156 | — |
| 10 | F-68 | 2.46 | 2.85 | 16.4 | 0.13 | — | 6.370 | 3.77 |
| 11 | F-68 | 3.09 | 2.46 | 27.9 | 0.09 | — | 5.520 | 16.6 |
| 12 | F-68 | 3.51 | 2.34 | 31.4 | 0.07 | — | 5.190 | 21.6 |
| 13 | F-68 | 3.51 | 2.44 | 28.5 | 0.08 | — | 5.466 | 17.4 |
| 14 | F-68 | 4.43 | 2.49 | 27.0 | 0.10 | — | 5.546 | 16.2 |
| 15 | F-127 | 1.68 | 2.51 | 26.4 | 0.08 | 77.6 | 5.652 | 14.6 |
| 16 | F-127 | 1.68 | 2.41 | 29.3 | 0.05 | 91.4 | 5.466 | 17.4 |
| 17 | F-127 | 2.57 | 2.51 | 26.4 | 0.06 | 89.7 | 5.652 | 14.6 |
| 18 | F-127 | 2.57 | 2.40 | 29.6 | 0.09 | 84.4 | 5.329 | 19.5 |
| 19 | F-127 | 4.16 | 2.53 | 25.8 | 0.07 | 87.9 | 5.782 | 12.7 |
| 20 | F-127 | 4.16 | 2.39 | 29.9 | 0.05 | 91.4 | 5.412 | 18.2 |
| 21 | F-127 | 5.16 | 2.48 | 27.3 | 0.06 | 89.7 | 5.626 | 15.0 |
| 22 | F-127 | 5.16 | 2.38 | 30.2 | 0.05 | 91.4 | 5.357 | 19.1 |
| 23 | F-127 | 5.95 | 2.45 | 28.2 | 0.10 | 82.8 | 5.412 | 18.2 |
| 24 | F-127 | 5.95 | 2.52 | 26.1 | 0.07 | 87.9 | 5.705 | 13.8 |
| 25 | F-127 | 5.95 | 2.43 | 28.7 | 0.04 | 93.1 | 5.520 | 16.6 |
| 26 | F-127 | 7.72 | 2.43 | 28.7 | 0.08 | 86.2 | 5.439 | 17.8 |

EXAMPLE 1

Friction and Chatter Tests

A set of 2/0 USP XIX (diameter 0.339 mm, maximum) braided silk sutures was coated with 5 levels of Pluronic F-68; and 12 levels of Pluronic F-127.

4 Blanks were run with no coating, on braid from the same lot, for comparison, and an average of these 4 used for comparative values.

With other braid constructions and other sizes, the relative ease of knot run-down may be greater or less for the same quantity of coating, or conversely the quantity of the coating may be adjusted to give the desired knot run-down values.

The quantity of the Pluronic in the solvent may be varied, and solvents other than chloroform may be used.

Other organic solvents such as methyl alcohol, ethyl alcohol, isopropyl alcohol, methylene chloride, warm xylene (about 60° C.), tetrahydrofuran, acetone, dimethylformamide, dimethyl sulfoxide, mixtures thereof, and other similar solvents for the lubricant may be used for coating. Flowing the solution onto a moving strand, and letting the surplus drip off is another useful coating technique.

A small amount of water increases the solubility of the lubricants, and aids in coating.

In general it is more convenient to use the solvent coating systems at levels below 10 percent pick-up and use a heated die at above about 10 percent pick-up.

EXAMPLE 2

2/0 Nylon Braided Sutures

Using the procedures described in Example 1, runs were made on nylon braid, sized for a 2/0 suture. The reduction in friction, and chatter factors are shown in Table IV. Both uncoated braids from the same lot, and commercial silicone coated nylon were used for comparison.

The reduction in chatter is particularly outstanding.

sizes of sutures. With different materials and constructions the results may vary.

The amount of coating and the ease of run-down can be varied to give results desired by the using surgeons.

For sutures, either absorbable or non-absorbable, in which capillarity is a problem, a coating of a phosphatide, preferably purified lecithin, such as taught by U.S. Pat. No. 2,576,576 may be used to reduce capillarity and friction, with the present coating as an additional friction reductant. Lecithin causes tissue irritation under some conditions, particularly if not pure.

EXAMPLE IV

A braided silk suture strand, of a size to form a 2/0 USP suture, is dipped in a 10% solution of Pluronic

TABLE IV

2/0 NYLON BRAID

| Pluronic Run No. | Level Coating | Static (%) | % Friction | % Chatter Reduction | % Factor | Coeff. of Reduction | % Friction × $10^{-2}$ | % Reduction |
|---|---|---|---|---|---|---|---|---|
| 1 | Blank | — | 3.02 | — | 0.33 | — | 6.300 | — |
| 2 | Blank | — | 2.89 | — | 0.53 | — | 6.205 | — |
| 3 | Blank | — | 3.06 | — | 0.51 | — | 5.933 | — |
| 4 | Silicone | — | 2.69 | 10.0 | 0.34 | 26.1 | 5.466 | 11.1 |
| 5 | Silicone | — | 2.89 | 3.34 | 0.42 | 8.69 | 5.762 | 6.25 |
| 6 | Silicone | — | 3.43 | — | 0.55 | — | 6.734 | — |
| 7 | F-68 | 2.53 | 2.24 | 25.1 | 0.18 | 60.9 | 4.632 | 24.6 |
| 8 | F-68 | 2.53 | 2.47 | 17.4 | 0.23 | 50.0 | 5.162 | 16.0 |
| 9 | F-68 | 2.53 | 2.43 | 18.7 | 0.16 | 65.2 | 5.218 | 15.1 |
| 10 | F-68 | 4.91 | 2.41 | 19.4 | 0.23 | 50.0 | 4.942 | 19.6 |
| 11 | F-68 | 5.60 | 2.29 | 23.4 | 0.18 | 60.9 | 4.726 | 23.1 |
| 12 | F-68 | 5.60 | 2.42 | 19.1 | 0.20 | 56.5 | 5.077 | 17.4 |
| 13 | F-68 | 5.60 | 2.46 | 17.1 | 0.17 | 63.0 | 5.274 | 14.2 |
| 14 | F-68 | 6.09 | 2.54 | 15.1 | 0.22 | 52.2 | 5.347 | 13.0 |
| 15 | F-127 | 2.83 | 2.49 | 16.7 | 0.19 | 58.7 | 5.302 | 13.7 |
| 16 | F-127 | 3.08 | 2.32 | 22.4 | 0.22 | 52.2 | 4.783 | 22.2 |
| 17 | F-127 | 3.36 | 2.36 | 21.1 | 0.17 | 63.0 | 4.989 | 18.8 |
| 18 | F-127 | 5.60 | 2.37 | 20.7 | 0.17 | 63.0 | 4.989 | 18.8 |
| 19 | F-127 | 5.60 | 2.36 | 21.1 | 0.12 | 73.9 | 5.133 | 16.5 |
| 20 | F-127 | 5.60 | 2.38 | 20.4 | 0.13 | 71.7 | 5.162 | 16.0 |
| 21 | F-127 | 6.21 | 2.37 | 20.7 | 0.15 | 67.4 | 5.077 | 17.4 |
| 22 | F-127 | 6.79 | 2.45 | 18.1 | 0.14 | 69.6 | 5.329 | 13.3 |
| 23 | F-127 | 7.57 | 2.65 | 11.4 | 0.28 | 39.1 | 5.520 | 10.2 |

EXAMPLE 3

2/0 Dacron ®Braid Sutures

Using the procedure of Example 1, runs were made on a polyester braid (Dacron ®) sized for a 2/0 suture. The reduction in friction and chatter factor are shown in Table V.

Both uncoated braid from the same lot and silicone coated braid were used for comparison. An average of the uncoated braid runs was used as a base to show improvement.

F-68 in chloroform, and dried. The pick up is about 5% by weight of the weight of the strand itself.

The dried coated strand is cut into 54 inch segments, needled, packaged, sterilized and dried in accordance with conventional procedures.

The thus prepared silk sutures are used in surgical procedures. When used to approximate tissue at a wound, a suture is placed in an appropriate location, and tied with a square knot. The square knot readily runs down to pull the edges of the wound to the degree of tightness desired by the using surgeon. The suture shows low tissue drag, and excellent knot run down.

TABLE V

2/0 Dacron Braid

| Run No. | Pluronic Coating | Level (%) | Static Friction | % Reduction | Chatter Factor | % Reduction | Coeff. of Friction × $10^{-2}$ | % Reduction |
|---|---|---|---|---|---|---|---|---|
| 1 | Blank | — | 2.89 | — | 0.31 | — | 6.027 | — |
| 2 | Blank | — | 2.65 | — | 0.34 | — | 5.310 | — |
| 3 | Blank | — | 2.54 | — | 0.28 | — | 5.189 | — |
| 4 | Silicone | — | 2.14 | — | 0.19 | — | 4.263 | — |
| 5 | Silicone | — | 2.20 | — | 0.17 | — | 4.478 | — |
| 6 | Silicone | — | 2.40 | — | 0.27 | — | 4.800 | — |
| 7 | F-127 | 2.39 | 2.60 | 3.45 | 0.33 | — | 5.216 | 5.30 |
| 8 | F-127 | 5.37 | 2.47 | 8.28 | 0.21 | 32.3 | 4.996 | 9.30 |
| 9 | F-127 | 5.12 | 2.36 | 12.4 | 0.21 | 32.3 | 4.871 | 11.6 |
| 10 | F-68 | 4.03 | 2.20 | 18.3 | 0.19 | 38.7 | 4.269 | 22.5 |
| 11 | F-68 | 4.03 | 2.28 | 15.3 | 0.21 | 32.3 | 4.628 | 16.0 |
| 12 | F-68 | 5.04 | 2.45 | 9.02 | 0.19 | 38.7 | 5.084 | 7.70 |
| 13 | F-68 | 6.26 | 2.24 | 16.8 | 0.18 | 41.9 | 4.580 | 16.8 |
| 14 | F-68 | 6.98 | 2.52 | 6.42 | 0.24 | 22.6 | 5.247 | 4.74 |
| 15 | F-68 | 8.59 | 2.26 | 16.1 | 0.14 | 54.8 | 4.785 | 13.1 |

The data in the example is illustrative. Reductions in frictions and improvement in chatter is obtained on all When a knot is at a desired final location, three additional squared throws are placed to secure the knot. Knots buried in tissue have the lubricant bioabsorbable copolymer removed from the suture surface within 48 hours, which gives additional knot security.

When removed from test animals after 48 hours, a square knot, without additional throws shows markedly greater knot security than immediately after placement.

In human tissue, in so far as can be observed, the knot security increases as the bioabsorbable lubricant coating is absorbed in tissue.

Whereas exemplified and tested with square knots, the ease of knot run-down and reduced tissue drag are useful in most suture placements and for knot retention. The amount of coating, and the relative values for knot run-down and reduced tissue drag, is variable to suit the requirement of a particular surgical situation.

The needling, packaging and sterilizing of the coated sutures is in accordance with conventional procedures.

We claim:

1. A non-absorbable surgical suture having improved knot run-down characteristics and reduced tissue drag comprising a polyfilamentary non-absorbable strand having thereon a thin lubricating coating of a lubricating absorbable co-polymer comprising polyoxyethylene blocks and polyoxypropylene blocks to aid run-down and handleability, said bioabsorbable copolymer having a molecular weight such that it is pasty to solid at 25° C.

2. The suture of claim 1 in which the lubricating bioabsorbable polymer has the formula:

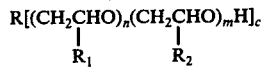

where one of $R_1$ and $R_2$ is methyl and the other hydrogen, and $n$ and $m$ are sufficiently large that the compound is pasty to solid at 25° C., R is the residue of a relatively low molecular weight reactive hydrogen compound having from 2 to about 6 reactive hydrogen atoms and having not over 6 carbon atoms in said compound, and $c$ is the number of reactive hydrogens on the compound forming R.

3. The suture of claim 1 in which the lubricating bioabsorbable copolymer has effectively the formula:

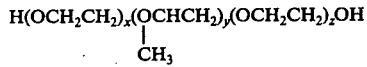

where $x$, $y$ and $z$ are sufficiently large that the lubricating bioabsorbable copolymer is pasty to solid at 25° C.

4. The suture of claim 3 in which the lubricating bioabsorbable copolymer has a moelcular weight of about 8350 and $x$ and $z$ are about 75 and $y$ about 30, and the melting point is about 52° C.

5. The suture of claim 1 in which the lubricating bioabsorbable copolymer has effectively the formula:

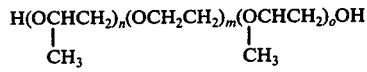

where $n$, $m$ and $o$ are sufficiently large that the lubricating bioabsorbable copolymer is pasty to solid at 25° C.

6. The suture of claim 1 in which the lubricating bioabsorbable copolymer has effectively the formula:

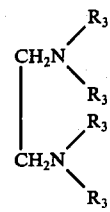

where $R_3$ is

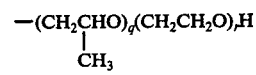

where $q$ and $r$ are sufficiently large that the lubricating bioabsorbable copolymer is pasty to solid at 25° C.

7. The suture of claim 1 in which the non-absorbable strand is selected from the group consisting of silk, cotton, nylon, a non-absorbable polyester, polypropylene and polyethylene.

8. The suture of claim 3 in which the non-absorbable strand is selected from the group consisting of silk, cotton, nylon, a non-absorbable polyester, polypropylene and polyethylene.

9. The suture of claim 4 in which the non-absorbable strand is selected from the group consisting of silk, cotton, nylon, a non-absorbable polyester, polypropylene and polyethylene.

10. The suture of claim 1 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

11. The suture of claim 2 in which the lubricating coating is about 0.1 to 25 percent by weight of the lubricating bioabsorbable copolymer of the weight of the uncoated strand forming the suture, whereby both chatter and fricion are reduced sufficiently that a square knot is movable on the suture with control of a wound edge.

12. The suture of claim 3 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

13. The suture of claim 4 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

14. The suture of claim 7 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

15. The suture of claim 8 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

16. The suture of claim 9 in which the lubricating coating is about 0.1 to 25 percent by weight of the lubricating bioabsorbable copolymer of the weight of the uncoated strand forming the suture, whereby both chatter and friction are reduced sufficiently that a square knot is movable on the suture with control of a wound edge.

17. A method of closing a wound in living tissue which comprises: sewing edges of a wound in living tissue with the sterile non-absorbable surgical suture of claim 1,
   tying the suture into a square knot,
   running down the square knot to approximate the tissues in a desired location,
   placing additional throws on the square knot, in a subcutaneous location, and
   within less than about 48 hours bioabsorbing and removing the lubricant absorbable coolymer from the suture thereby increasing knot security, and
   leaving the non-absorbable surgical suture in living tissue, thereby reinforcing the tissue.

* * * * *

UNITED STATES PATENT OFFICE
CERTIFICATE OF CORRECTION

Patent No. 4,043,344           Dated August 23, 1977

Inventor(s) Henry Patrick Landi, et al

It is certified that error appears in the above-identified patent and that said Letters Patent are hereby corrected as shown below:

At Column 13 & 14, Table IV, delete the heading as shown and substitute the attached heading therefor.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*

TABLE IV
2/0 NYLON BRAID

| Run No. | Pluronic Coating | Level (%) | Static Friction | % Reduction | Chatter Factor | % Reduction | Coeff. of Friction x $10^{-2}$ | % Reduction |
|---|---|---|---|---|---|---|---|---|

UNITED STATES PATENT OFFICE
CERTIFICATE OF CORRECTION

Patent No. 4,043,344　　　Dated August 23, 1977

Inventor(s) Henry Patrick Landi et al.

It is certified that error appears in the above-identified patent and that said Letters Patent are hereby corrected as shown below:

Column 5, lines 47 - 50 and Column 15, Claim 3, lines 46 - 50, the formula, each occurrence, should appear as shown below:

Column 6, lines 1 - 5 and Column 15, Claim 5, lines 60 - 64, the formula, each occurrence, should appear as shown below:

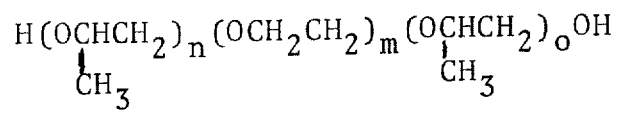

UNITED STATES PATENT OFFICE
CERTIFICATE OF CORRECTION

Patent No. 4,043,344    Dated August 23, 1977

Inventor(s) Henry Patrick Landi et al.

It is certified that error appears in the above-identified patent and that said Letters Patent are hereby corrected as shown below:

Columns 7 and 8, under the heading "Table I - continued" delete "M. W. polyethylene units of m block" and add -- M. W. of polyoxyethylene units of m block --.

Signed and Sealed this

Eighteenth Day of April 1978

[SEAL]

Attest:

RUTH C. MASON
Attesting Officer

LUTRELLE F. PARKER
Acting Commissioner of Patents and Trademarks